United States Patent [19]

Taub et al.

[11] 3,992,413

[45] Nov. 16, 1976

[54] INTERMEDIATES IN THE SYNTHESIS OF PROSTAGLANDINS

[75] Inventors: David Taub, Metuchen; Norman L. Wendler, Summit, both of N.J.

[73] Assignee: Merck & Co., Inc., Rahway, N.J.

[22] Filed: July 25, 1975

[21] Appl. No.: 599,202

[52] U.S. Cl. .............................. 260/340.9; 260/309; 260/343; 260/343.3 R; 260/413; 260/514 D
[51] Int. Cl.$^2$ ...................................... C07D 317/72
[58] Field of Search ............................. 260/340.9 P

[56] References Cited
UNITED STATES PATENTS
3,833,612   9/1974   Wendler et al. .............. 260/340.9 P

*Primary Examiner*—Ethel G. Love
*Attorney, Agent, or Firm*—Thomas E. Arther; Harry E. Westlake, Jr.; Rudolph J. Anderson, Jr.

[57] ABSTRACT

The invention relates to a new and novel synthesis of prostaglandin $E_2$, and it particularly relates to a novel process starting with relatively inexpensive starting materials. The invention further relates to a synthesis which is readily adaptable for large scale processing because of the high yields in the individual reaction steps.

The invention further relates to novel compounds formed as intermediates in the synthesis of prostaglandin $E_2$. The invention still further relates to synthetic analogs and known metabolites of prostaglandin $E_2$ and prostaglandin $E_1$, useful as standards in certain biological assays for determining prostaglandin-like activity.

3 Claims, No Drawings

INTERMEDIATES IN THE SYNTHESIS OF PROSTAGLANDINS

DETAILED DESCRIPTION OF THE INVENTION

Prostaglandin $E_2$, which may be depicted structurally as

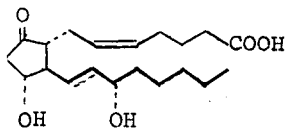

is one of a group of naturally-occurring compounds known as prostaglandins. These prostaglandins have interesting and important biological activities, the precise biological activities varying with the individual members of the prostaglandin family as described the article, "Prostaglandins" by P. W. Ramwell, Plenum Press (1973).

One of the more important prostaglandins is prostaglandin $E_2$. It has an effect on the contractility of smooth muscle and is useful in the induction of labor in pregnant females and for the termination of pregnancy by therapeutic abortion. It also reduces pentagastrin-induced gastric secretion in laboratory test animals and is therefore potentially useful in the control and treatment of gastric ulcers in humans. It is also effective in increasing nasal patency and is therefore useful in the treatment of symptoms of allergic rhinitis.

Another substance of related structure produced in accordance with the processes of our invention is $7\alpha$-hydroxy-5,11-diketo-tetranor-prostane-1,16-dioic acid, which is the major urinary metabolite of both prostaglandin $E_1$ and $E_2$. This substance, when prepared by the synthesis disclosed herein, may have isotopic elements incorporated into its structure, thus making available a major molecule which may be used in isotope dilution assays useful in evaluating biological systems. Thus, for example, it is of value in estimating the potency of certain antiinflammatory agents to measure the inhibition of prostaglandin production and the consequent inhibition of the metabolic products produced in laboratory animals and/or humans.

Heretofore, the supply of prostaglandin $E_2$ has been limited because only very small amounts of naturally-occurring material are available by various extraction methods, and partial biosynthesis by enzymes present in mammalian seminal vesicles has only afforded small amounts of product. More recently, the material has been produced by total synthesis from commercially-available starting materials. In addition, isotopically-labelled $7\alpha$-hydroxy-5,11-diketo-tetranor-prosta-1,16-dioic acid has been available in very limited amounts by isolation from urine following administration of isotopically-labelled prostaglandins.

An object of this invention is to provide a novel and economical synthesis of racemic prostaglandin $E_2$ as well as naturally-occurring prostaglandin $E_2$. The racemic compound has one half the biological activity of the naturally-occurring prostaglandin $E_2$.

A further object of this invention is to provide novel intermediates; some of which, in addition to being useful in the synthesis of prostaglandin $E_2$, may themselves possess useful biological activity similar to the naturally-occurring prostaglandins.

A still further object of the invention is to provide processes for the preparation of known metabolites of prostaglandin $E_1$ and prostaglandin $E_2$, which are useful as biological standards for laboratory assays.

A still further object of the present invention is to provide a stereoselective total synthesis of prostaglandin $E_2$ and one of the major urinary metabolites thereof, beginning with $\beta$-angelica lactone and butadiene as starting materials.

The novel processes and intermediates of our invention are shown structurally in the following flow diagram, and immediately following this diagram, the chemical names of the compounds are set forth.

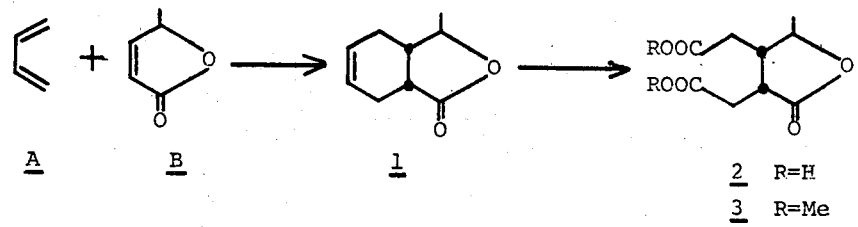

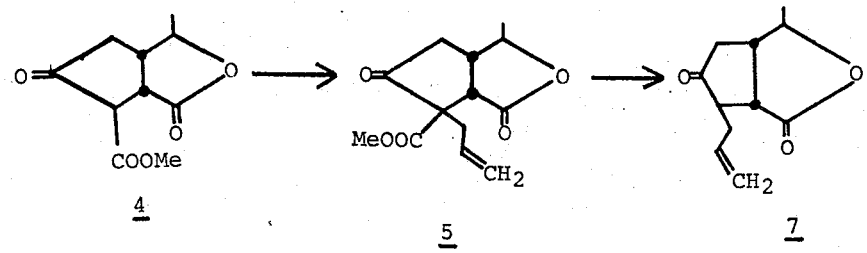

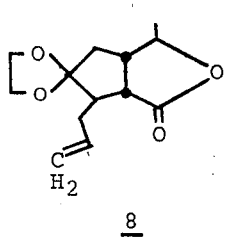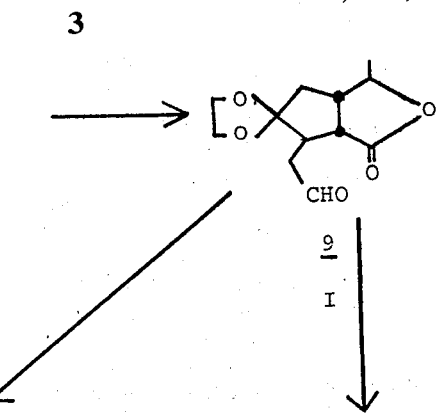
8
9
I
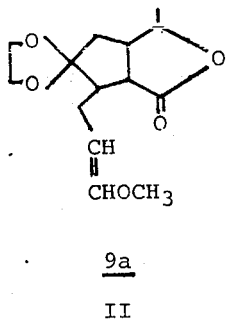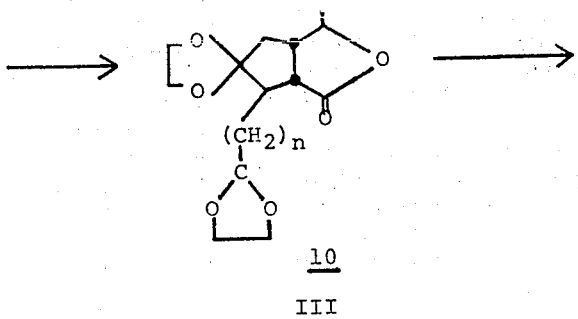
9a
II
10
III
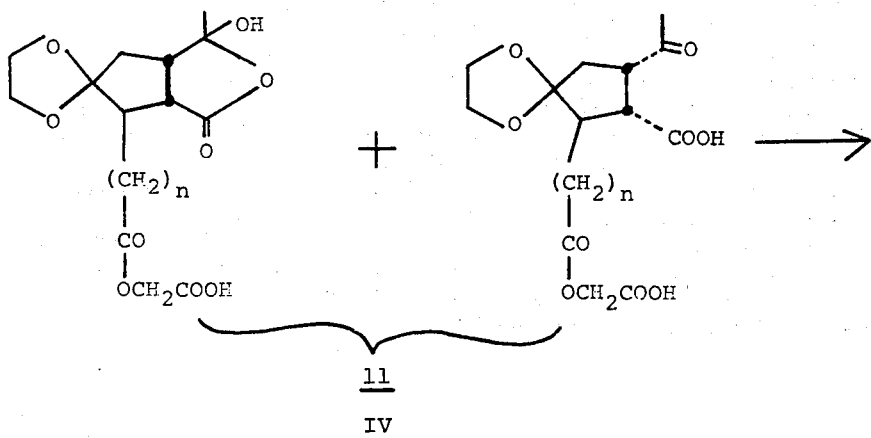
11
IV
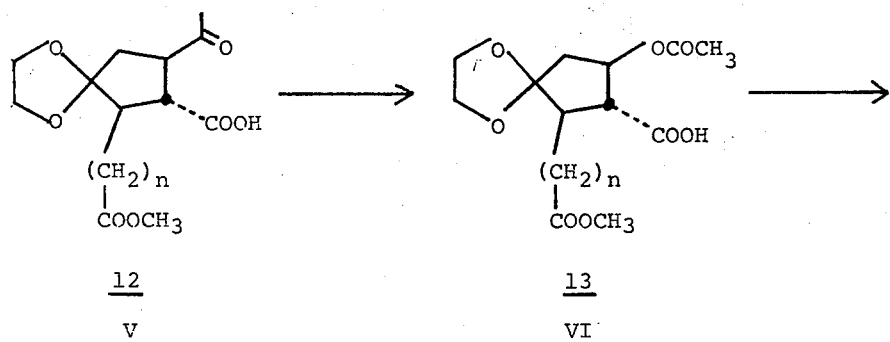
12
V
13
VI
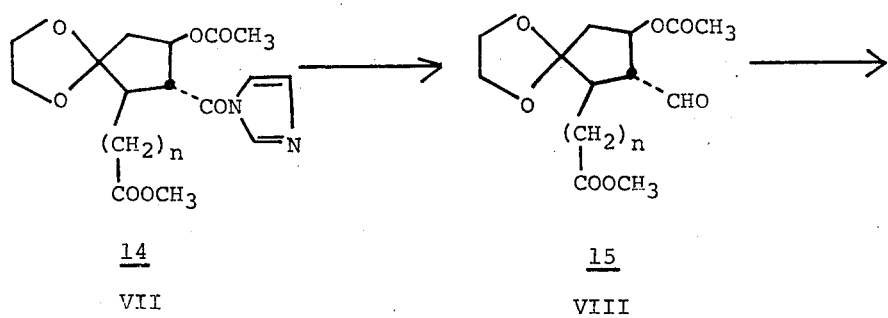
14
VII
15
VIII

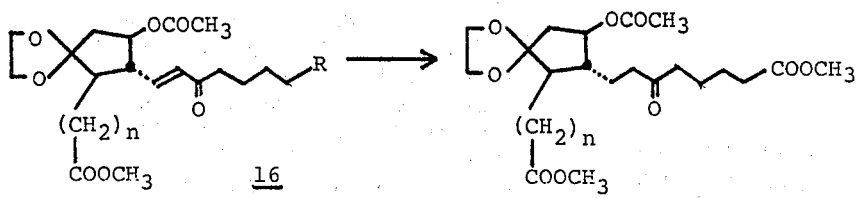
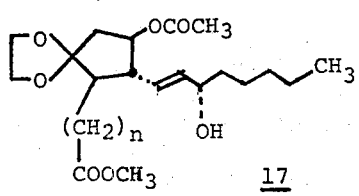
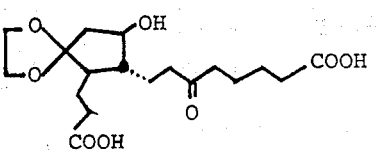
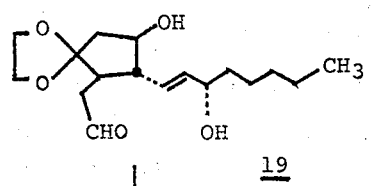
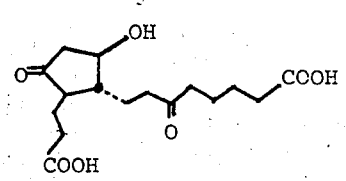
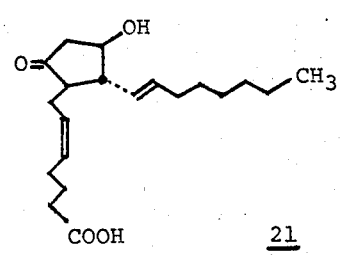
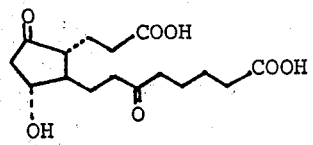
7α-hydroxy-5,11-diketo-tetranor-prosta-1,16-dioic acid
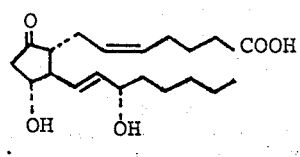
PGE$_2$ In the formulae hereinabove,
n is 1 or 2, and
R$^1$ is methyl or -COOCH$_3$.

As a matter of convenience for understanding the preceeding flowsheet and the following description, there follows a list of names of the chemical compounds disclosed.

A = butadiene
B = β angelica lactone

1 = 2α-carboxy-1α(1-hydroxyethyl)-4-cyclohexene, lactone

2 = cis 2,3-dicarboxymethyl-4-methylbutyrolactone

3 = cis 2,3-dicarboxymethyl-4-methylbutyrolactone, dimethyl ester

4 = 1-carbomethoxy-2α-carboxy-3α-(1-hydroxyethyl)-5-oxocyclopentane γ-lactone

5 = 1-carbomethoxy-1-allyl-2α-carboxy-3α-(1-hydroxyethyl)-5-oxocyclopentane γ-lactone 7 = 1-allyl-2α-carboxy-3α-(1-hydroxyethyl)-5-oxocyclopentane γ-lactone 8 = 1-allyl-2α-carboxy-3α-(1-hydroxyethyl)-5-oxocyclopentane-5-cyclic ethylene acetal-γ-lactone 9 = 1-formylmethyl-2α-carboxy-3α-(1-hydroxyethyl)-5-oxo-cyclopentane-5-cyclic ethylene acetal, γ-lactone 9a = 2α-carboxy-3α-(1-hydroxyethyl)-1-(3-methoxy-2-propenyl)-5-oxocyclopentane-5-cyclic ethylene acetal-γ-lactone 10 = 2α-carboxy-3α-(1-hydroxyethyl)-1-(3-ethylenedioxypropyl)-5-oxocyclopentane-5-cyclic ethylene acetal where n = 2
or
2α-carboxy-3α-(1-hydroxyethyl)-1-(2-ethylenedioxy-ethyl)-5-oxocyclopentane-5-cyclic ethylene acetal where n = 1

11 = where n = 1
2α-carboxy-3α-(1,1-dihydroxyethyl)-5-oxocyclopentane acetic acid methylester, γ-lactone-5-cyclic ethylene acetal and
3α-acetyl-2α-carboxy-5-oxo-1β-cyclopentane acetic acid methylester-5-cyclic ethylene acetal 12 = where n = 1
3β-acetyl-2α-carboxy-5-oxo-cyclopentane-1β-acetic acid, methylester 5-cyclic ethylene acetal 13 = where n = 1
3β-acetoxy-2α-carboxy-5-oxo-cyclopentane-1β-acetic acid, methyl ester 5-cyclic ethylene acetal 14 = where n = 1
3β-acetoxy-2α-imidazoylformyl-5 -oxo-cyclopentane-1β-acetic acid, methyl ester 5-cyclic ethylene acetal 15 = where n = 1
3β-acetoxy-2α-formyl-5-oxocyclopentane-1β-acetic acid, methyl ester 5-cyclic ethylene acetal 16 = where n = 1 and R$^1$ = CH$_3$
3β-acetoxy-2-(3-oxo-1-octenyl)-5-oxocyclopentane-1β-acetic acid, methyl ester 5-cyclic ethylene acetal
where n = 2 and R$^1$ = COOCH$_3$
3β-acetoxy-2-(7-carbomethoxy-3-oxo-1-heptenyl)-5-oxocyclopentane-1β-propionic acid, methyl ester 5-cyclic ethylene acetal 17 = 3β-acetoxy-2α-(3-hydroxy-1-octenyl)-5-oxocyclopentane-1β-acetic acid, methyl ester 5-cyclic ethylene acetal 19 = 3β-hydroxy-2α-(3-hydroxy-1-octenyl)-5-oxocyclopentane-1β-acetaldehyde, 5-cyclic ethylene acetal XI = 3β-acetoxy-2α-(7-carbomethoxy-3-oxo-heptanyl)-5-oxocyclopentane-1β-propionic acid, methyl ester 5-cyclic ethylene acetal XII = 3β-hydroxy-2α-(7-carbomethoxy-3-oxo-heptanyl)-5-oxocyclopentane-1β-propionic acid 5-cyclic ethylene acetal XIII = 7α-hydroxy-5,11-diketo-tetranorprosta-1,16-dioic acid.

The synthesis of (±) prostaglandin E$_2$, the prostaglandin intermediate (±) XIII, or the corresponding optical isomers having the natural configuration starts with the condensation of butadiene (A) and β-angelica lactone (B) in a Diels-Alder reaction. The reaction is generally run in a closed reaction vessel with the preferred temperature in the 150°–250° C. range. A solvent is optional as the reaction is readily performed without one; however, if one is employed, a non-reactive aprotic solvent is preferred. In general, however, the only need for a solvent is to facilitate the transfer of the reactants into the reaction vessel. The reaction is generally complete in from 5 to 50 hours in the above temperature range. Preferably, the reaction is run at from 20 to 30 hours at 175°–225° C.

The Diels-Alder adduct, 2α-carboxy-1α(1-hydroxyethyl)-4-cyclohexene lactone is treated with an oxidizing agent capable of selectively cleaving an olefinic bond in order to oxidatively cleave the cyclohexene double bond and form the dicarboxylic acid, cis 2,3-dicarboxymethyl-4-methyl butyrolactone. The oxidizing agents of choice are ozone, potassium permanganate, sodium periodate-potassium permanganate, and the like. Ozonolysis is the preferred procedure. Owing to the reactivity of ozone, the reaction is run at a depressed temperature of from −20 to −80° C. The ozonide intermediate is decomposed by treatment with hydrogen peroxide in acetic acid at from 25°–75° C. The product is isolated by techniques known to those skilled in this art.

The dicarboxy acid, cis 2,3-dicarboxymethyl-4-methylbutyrolactone, is converted to the corresponding diloweralkyl ester by procedures known to those skilled in the art, e.g., by heating at reflux temperature in the presence of an excess of lower C$_1$–C$_5$ alkanol and a small amount of a strong acid to produce the corresponding cis 2,3-dicarboxymethyl-4-methyl-butyrolactone, di-C$_1$–C$_5$ lower alkyl ester.

The thus-produced diloweralkyl ester is heated in the presence of a base such as an alkali metal alkoxide, preferably sodium tert-amylate in an inert solvent at 40°–80° C. for from 10 minutes to about 1 hour to effect ring closure and produce, following acidification and extraction, 1-carbomethoxy-2α-carboxy-3α-(1-hydroxyethyl)-5-oxocyclopentane γ-lactone.

The lactone, 1-carbomethoxy-2α-carboxy-3α-(1-hydroxyethyl)-5-oxocyclopentane γ-lactone, is then alkylated using a solution of an alkali metal alkoxide, preferably sodium tert. amylate in benzene, then refluxed with allyl bromide for a period of from 1–24 hours to produce 1-carbomethoxy-1-allyl-2α-carboxy- 3α-(1-hydroxyethyl)-5-oxocyclopentane γ-lactone.

Rearrangement and decarbomethoxylation of 1-carbomethoxy-1-allyl-2α-carboxy-3α-(1-hydroxyethyl)-5-oxocyclopentane γ-lactone to produce 1-allyl-2α-carboxy-3α-(1-hydroxyethyl)-5-oxocyclopentane γ-lactone is readily accomplished by first refluxing the allyl substituted ester in the presence of sodium methoxide in methanol for a period of from 30 minutes to about 5 hours followed by careful acidification of the resulting sodium enolate to produce the desired β-keto ester 1-allyl-4-carbomethoxy-2α-carboxy-3α(1-hydroxyethyl)-5-oxocyclopentane-γ-lactone.

The resultant product is then decarbomethoxylated by heating in the presence of aqueous sodium chloride to produce 1-allyl-2α-carboxy-3α(1-hydroxyethyl)-5-oxocyclopentane γ-lactone.

The allyl ketolactone is then ketalized with ethylene glycol and p-toluene sulfonic acid and the allyl double bond ozonized in the manner described above to produce the aldehyde 1-formylmethyl-2α-carboxy-3α-(1-hydroxyethyl)-5-oxocyclopentane-5-cyclic ethylene acetal, γ-lactone.

The aldehyde is then reacted with ethylene glycol in the presence of p-toluene sulfonic acid to produce 2α-carboxy-3α-(1-hydroxyethyl)-1-(2-ethylenedioxyethyl)-5-oxo-5-cyclic ethylene acetal γ-lactone. Alternatively, the aldehyde is contacted with the phosphorane derived from methoxy methyl triphenyl phosphonium chloride and a base such as butyl lithium to form 2α-carboxy-3α-(1-hydroxyethyl)-1-(3-methoxy-2-propenyl)-5-oxo-5-cyclic ethylene acetal-γ-lactone, which is then acetalized with ethylene glycol to form the homologous 2α-carboxy-3α-(1-hydroxyethyl)-1-(3-ethylenedioxypropyl)-5-oxo-5-cyclic ethylene acetal γ-lactone.

The intermediate 2α-carboxy-3α-(1-hydroxyethyl)-1-(2-ethylenedioxyethyl)-5-oxo-5-cyclic ethylene acetal γ-lactone or the next higher homolog is then oxidized at a pH of 8–9, preferably using ruthenium dioxide and sodium periodate in water, affording a mixture of 2α-carboxy-3α-(1,1-dihydroxyethyl)-5-oxo-1β-cyclopentane acetic acid, methyl ester, γ-lactone-5-cyclic ethylene acetal and 3α-acetyl-2α-carboxy-5-oxo-1β-cyclopentane acetic acid methyl ester-5-cyclic ethylene acetal or the propionic acid homolog.

Treatment of 3α-acetyl-2α-carboxy-5-oxo-1β-cyclopentane acetic acid methyl ester-5-cyclic ethylene acetal or the next higher homolog with sodium methoxide in methanol for a period of from 5–24 hours produces 3β-acetyl-2α-carboxy-5-oxo-cyclopentane-1β-acetic acid, methyl ester 5-cyclic ethylene acetal or the corresponding propionic acid compound, each of which is selectively oxidized using peroxytrifluoroacetic acid in methylene dichloride buffered with disodium hydrogen phosphate to produce 3β-acetoxy-2α-carboxy-5-oxo-cyclopentane-1β-acetic acid, methyl ester 5-cyclic ethylene acetal or 3β-acetoxy-2α-carboxy-5-oxocyclopentane-1β-propionic acid, methyl ester 5-cyclic ethylene acetal.

Each of these acetoxy monoesters is converted to the corresponding imidazolide which is in turn reduced at 25° C. using lithium-tri-t-butoxy aluminum hydride to 3β-acetoxy-2α-formyl-5-oxocyclopentane-1β-acetic acid, methyl ester 5-cyclic ethylene acetal or 3β-acetoxy-2α-formyl-5-oxocyclopentane-1β-propionic acid, methyl ester 5-cyclic ethylene acetal. These aldehydes are then respectively reacted under Wittig reaction conditions with dimethyl 2-oxoheptylphosphonate and a base to produce 3β-acetoxy-2α-(3-oxo-1-octenyl)-5-oxocyclopentane-1β-acetic acid, methyl ester 5-cyclic ethylene acetal and with dimethoxy 2-oxo-6-carbomethoxy-n-hexylphosphonate and a base to produce 3β-acetoxy-2α-(7-carbomethoxy-3-oxo-1-heptenyl)-5-oxocyclopentane-1β-propionic acid, methyl ester 5-cyclic ethylene acetal.

3β-Acetoxy-2α-(3-oxo-1-octenyl)-5-oxocyclopentane-1β-acetic acid, methyl ester 5-cyclic ethylene acetal is converted to prostaglandin $E_2$ by hydrolysis of the acetoxy substituent conversion to the imidazolide and reduction to the aldehyde 3β-hydroxy-2α-(3-hydroxy-1-octenyl)-5-oxocyclopentane-1β-acetaldehyde, 5-cyclic ethylene acetal, as described hereinabove.

The resulting aldehyde is then readily converted to ± prostaglandin $E_2$ by reaction with sodium hydride in diemthyl sulfoxide and 4-carboxybutyltriphenylphosphonium bromide followed by removal of the acetal function using dilute acid.

The urinary metabolite (±) 7α-hydroxy-5,11-diketotetranorprostane-1,16-dioic acid is produced from the homologous intermediates beginning with catalytic hydrogenation of 3β-acetoxy-2α-(7-carbomethoxy-3-oxo-1-heptenyl)-5-oxocyclopentane-1β-propionic acid, methyl ester 5-cyclic ethylene acetal to produce 3β-acetoxy-2α-(7-carbomethoxy-3-oxoheptanyl)-5-oxocyclopentane-1β-propionic acid, methyl ester 5-cyclic ethylene acetal, followed by saponification to the diacid, 3β-hydroxy-2α-(7-carboxy-3-oxo-heptanyl)-5-oxocyclopentane-1β-propionic acid 5-cyclic ethylene acetal. The acetal function is then removed in the manner previously described for the prostaglandin $E_2$ series to produce ± 7α-hydroxy-5,11-diketo-tetranor-prostane-1,16-dioic acid.

The above procedure is readily repeated using deuterium in place of hydrogen to saturate the side chain double bond with two deuterium atoms. Additional deuterium and tritium atoms are substituted for the hydrogens of the carbons adjacent to the side chain carbonyl substituent by carrying out the saponification reaction with a mixture of potassium deuterooxide and potassium tritiooxide in deuteromethanol-0-d and tritiomethanol-0-t.

In the synthesis described above, there are produced racemic (±) prostaglandin $E_2$ and racemic (±) metabolite. The corresponding compounds having the natural configuration are produced by the optical resolution of one of the earlier intermediates in the synthesis. Thus, for example, 3β-acetyl-2α-carboxy-5-oxo-cyclopentane-1β-acetic acid, methylester 5-cyclic ethylene acetal is reacted with an optical isomer of an optically-active amine, e.g., (−) α-methylbenzylamine, to form the corresponding diastereoisomeric salt. The thus-formed salt is recrystallized and the isomer of the above intermediate having the configuration of the natural product is produced. The isomer having the natural configuration is converted to prostaglandin $E_2$ having the natural configuration by repetition of the synthesis carried out for the racemic compound. The same procedure utilizing (−) ephedrine as the optically-active amine is employed for the next higher homolog, 3β-acetyl-2α-carboxy-5-oxocyclopentane-1β-propionic acid, methyl ester 5-cyclic ethylene acetal, with resultant production of urinary metabolite 7α-hydroxy-5,11-diketo-tetranor-prostane-1,16-dioic acid.

In the following examples, temperatures are in degrees centigrade; and starting materials and products are referred to by numerals shown in the foregoing flowsheet.

EXAMPLE 1

2α-Carboxy-1α(1-hydroxyethyl)-4-cyclohexene, lactone

A + B → 1

A mixture of 90 g. β-angelica lactone (~95% -- contains ~5% α-angelica lactone), 325 ml. of butadiene, 50 ml. of xylene, and 50 mg. hydroquinone in a glass-lined autoclave is kept at 200° for 24 hours. The adduct 1 is purified by vacuum distillation: 92.5 g. (66%) b.p. 75°/0.1 mm.; vpc ret. time 4.0 minutes (20% OV101, 195°); m/e 152; $\lambda_{max}^{chf}$ 5.65μ; nmr ε1.38 (3H, d, J=6), 4.25 (1H, q, J=6, d, J=2), 580 (2H, broad s).

EXAMPLE 2

Cis 2,3-dicarboxymethyl-4-methylbutyrolactone

1 → 2

A solution of 2α-carboxy-1α(1-hydroxyethyl)-4-cyclohexene, lactone (20.0 g.) in methylene chloride (500 ml.) cooled to ~−75° is ozonized (ca 5% $O_3$ in $O_2$) until excess ozone is visible (blue color). Excess ozone is swept out with nitrogen and the solution is concentrated under vacuum to a viscous foam. The residue is dissolved in acetic acid (350 ml.) and 30% hydrogen peroxide (150 ml.), and the mixture is stirred at 65° for 18 hours. The solution is concentrated to dryness under vacuum and the last traces of acetic acid removed by flushing with toluene and concentrating to dryness until a solid residue is obtained. The latter is suspended in ethyl acetate (100 ml.), the mixture chilled to ~15° and $SO_2$ cautiously bubbled in with stirring until a negative peroxide test (moist starch-iodide paper) is obtained. The product 2 is filtered and washed with ether, 25.0 g. (88%) m.p. 162–165°.

EXAMPLE 3

Cis 2,3-dicarboxymethyl-4-methylbutyrolactone, dimethyl ester

2 → 3

A solution of 10 g. of cis 2,3-dicarboxymethyl-4-methylbutyrolactone in methanol (100 ml.) and conc. sulfuric acid (0.2 ml.) is refluxed for 2 hours. The mixture is concentrated on the water pump to a volume of 10–15 ml., sat. aq. $KHCO_3$ is added and it is extracted with ether. The ether extract is washed with sat. aq. NaCl, dried over $MgSO_4$, and concentrated to dryness to give the dimethyl ester 3 (11.0 g.) which crystallizes spontaneously; m.p. 56°–57.5° (from ether); ir ($CHCl_3$) 5.65, 5.78μ; nmr ($CDCl_3$) δ1.44 (3H, d, J=7), 3.70 (3H, s), 3.73 (3H, s), 4.47 (1H, q, J=7); m/e 244.

EXAMPLE 4

1-Carbomethoxy-2α-carboxy-3α-(1-hydroxyethyl)-5-oxocyclopentane γ-lactone

3 → 4

To a stirred solution of sodium tert-amylate in benzene (230 ml. of 0.43M) maintained at 50°–60° under nitrogen is added over 20 minutes 22 g. of cis 2,3-dicarboxymethyl-4-methylbutyrolactone, dimethyl ester in 125 ml. of benzene. The mixture is cooled to room temperature, stirred 30 minutes, and the precipitated sodium enolate filtered and washed with benzene. The precipitate is partitioned between ethyl acetate (100 ml.) and cold 1N HCl (100 ml.). The mixture is extracted five times with ethyl acetate (until a $FeCl_3$ test is negative). The organic extract is washed once with sat. aq. NaCl, dried over $MgSO_4$, and concentrated to dryness under vacuum. Crystallization of the residue from ether yields 1-carbomethoxy-2α-carboxy-3α-(1-hydroxyethyl)-5-oxocyclopentane γ-lactone (8.10 g.) m.p. 81°–86° raised to 88°–90° on recrystallization from acetone-ether.

Treatment of the residual material (11.0 g.) in methanol (10 ml.) and ether (10 ml.) with excess ethereal diazomethane concentration to dryness after 4 hours, and crystallization of the residue from ether yields the corresponding enol ether I (2.76 g.) m.p. 130°–132°; ir ($CHCl_3$) 5.67, 5.88, 6.1μ; nmr ($CDCl_3$) δ1.38 (3H, d, J=7); 3.73 (3H, s), 3.80 (3H, s); m/e 226.

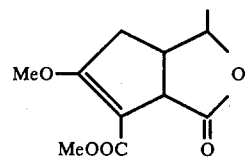

I

The enol methyl ether I (2.76 g.) is kept in acetone (20 ml.) and 1N hydrochloric acid (30 ml.) at room temperature for 4 hours. The solution is concentrated under vacuum to remove the acetone, solid NaCl is added and the mixture extracted with ethyl acetate. The latter extract is dried over $MgSO_4$ and taken to dryness under vacuum to give 2.72 g. of solid usuable 1-carbomethoxy-2α-carboxy-3α-(1-hydroxyethyl)-5-oxocyclopentane γ-lactone (total yield 10.8 g. - 57%); vpc (20% OV101; 235°) shows complete conversion to β-keto ester.

EXAMPLE 5

1-Carbomethoxy-1-allyl-2α-carboxy-3α-(1-hydroxyethyl)-5-oxocyclopentane γ-lactone

4 → 5

To a stirred solution of sodium tert-amylate in benzene (80 ml. of 0.43M) maintained at 50°–60° under nitrogen is added over 5 minutes 6.65 g. of 1-carbomethoxy-2α-carboxy-3α-(1-hydroxyethyl)-5-oxocyclopentane γ-lactone in 20 ml. of benzene. To the stirred precipitated sodium enolate is added 30 ml. of allyl bromide (5 min.) and the mixture is refluxed overnight. It is then cooled, concentrated to dryness under vacuum, and partitioned between water and $CHCl_3$. The mixture is extracted three times with $CHCl_3$, and the organic extract washed with sat. aq. NaCl, dried over $MgSO_4$, and concentrated to dryness under vacuum. Crystallization of the residue from ether yields 1-carbomethoxy-1-allyl-2α-carboxy-3α-(1-hydroxyethyl)-5-oxocyclopentane γ-lactone: 4.97 g. (63%) m.p. 88°–90°; ir $(CHCl_3)$ 5.65, 5.75, 5.80, 6.1μ; nmr $(CDCl_3)$ δ1.45 (3H, d, J=6), 3.67 (3H, s), 4.46 (1H, m), 4.9–6.0 (3H, m); ((−)$FeCl_3$ test).

EXAMPLE 6

1-allyl-2α-carboxy-3α-(1-hydroxyethyl)-5-oxocyclopentane γ-lactone

5 → 6

To a stirred solution under nitrogen of 1-carbomethoxy-1-allyl-2α-carboxy-3α-(1-hydroxyethyl)-5-oxocyclopentane γ-lactone (4.54 g.) in 10 ml. of dry benzene is added 30 ml. of dry methanol and 5.6 ml. of 3.26M sodium methoxide in methanol. The mixture is refluxed one hour. A total of 80 ml. of dry benzene is added in 20 ml. increments with slow distillation of solvent. The gradual replacement of methanol by benzene is continued until the Na enolate of 6 precipitates as a gummy solid. The mixture is cooled, the solvent decanted, and the residue partitioned between ethyl acetate and sat. aq. $NaH_2PO_4$. The aqueous phase is extracted 4 times with ethyl acetate, the latter extract is dried over $MgSO_4$ and taken to dryness under vacuum to give 1-allyl-4-carbomethoxy-2α-carboxy-3α-(1-hydroxyethyl)-5-oxocyclopentane-γ-lactone (6) (4.5 g.) as a pale yellow oil ((+)$FeCl_3$ test).

6 → 7

A solution of allyl ester 6 (2.00 g.) in dimethyl formamide (6 ml.) and water (0.6 ml.) containing 0.50 g. of sodium chloride is heated at 120° for 3 hours under nitrogen. The mixture is concentrated to dryness under vacuum. The residue is taken up in ether, the insoluble material removed by filtration, and the ether solution taken to dryness to yield 1-allyl-2α-carboxy-3α-(1-hydroxyethyl)-5-oxocyclopentane γ-lactone (1.54 g.) which crystallizes on cooling m.p. 27°–29°; ir $(CHCl_3)$ 5.68, 5.75, 6.15μ; nmr $(CDCl_3)$ δ1.45 (3H, d, J=7), 4.43 (1H, q of d, J=7,3), 5.0–5.4 (2H, m), 5.45–6.1 (1H, m); 2,4-dinitrophenylhydrazone, m.p. 185°–187°.

EXAMPLE 7

1-allyl-2α-carboxy-3α-(1-hydroxyethyl)-5-oxocyclopentane-5-cyclic ethylene acetal-γ-lactone

7 → 8

A solution of 1-allyl-2α-carboxy-3α-(1-hydroxyethyl)-5-oxocyclopentane γ-lactone (2.16 g.) in 100 ml. benzene, 5 ml. of ethylene glycol and 50 mg. of p-toluene-sulfonic acid is refluxed overnight with separation of the water formed. The mixture is cooled, extracted with dilute aq. $KHCO_3$, sat. aq. NaCl, dried over $Na_2SO_4$, and concentrated to dryness under vacuum to yield 1-allyl-2α-carboxy-3α-(1-hydroxyethyl)-5-oxocyclopentane-5-cyclic ethylene acetal-γ-lactone (2.46 g.) m.p. 31°–33° (from ether-hexane); ir $(CHCl_3)$ 5.65, 6.1, 10.55μ.

EXAMPLE 8

1-Formylmethyl-2α-carboxy-3α-(1-hydroxyethyl)-5-oxocyclopentane-5-cyclic ethylene acetal, γ-lactone
and
2α-carboxy-3α-(1-hydroxyethyl)-1-(2-ethylenedioxyethyl)-5-oxocyclopentane-5-cyclic ethylene acetal

8 → 9 → 10

A solution of 1-allyl-2α-carboxy-3α-(1-hydroxyethyl)-5-oxocyclopentane-5-cyclic ethylene acetal-γ-lactone (2.18 g.) in 70 ml. of methanol is ozonized at −78° until the blue color of dissolved ozone is visible. Excess ozone is displaced by nitrogen and dimethyl sulfide (2.5 ml.) is added. The mixture is kept 30 min. at −78°, 30 min. at 0°, and 17 hours at room temperature. It is concentrated to dryness, taken up in EtOAc-φH 1:1, and the latter solution washed 3 times with sat. aq. NaCl, dried over $Na_2SO_4$, and concentrated to dryness to yield the aldehyde 9 (2.20 g.) as a pale yellow oil: ir $(CHCl_3)$ 3.65, 5.65, 5.79, 10.55μ.

Treatment of 9 with ethylene glycol as in the previous experiment yields the bis-acetal 10; ir $(CHCl_3)$ 5.65, 10.30, 10.55μ; nmr $(CDCl_3)$ δ1.37 (3H, d, J=6), 3.83 (8H, broad s), 4.27 (1H, q, J=6, d, J=2), 5.00 (1H, t, J=4); m/e 284.

EXAMPLE 8a

2α-Carboxy-3α-(1-hydroxyethyl)-1-(3-methoxy-2-propenyl)-5-oxocyclopentane-5-cyclic ethylene acetal γ-lactone

I=9 → II

To a stirred solution (t = 0°–10°) of diisopropyl amine (4.2 ml.) in 100 ml. of benzene under $N_2$ is added 15 ml. of 2M n-butyl lithium. After 10 minutes, 10.3 g. of methoxymethyl triphenylphosphonium chloride is added portionwise (2 min.), and the mixture is stirred at ~25° for 2 hours. To the deep-red solution of methoxymethylene triphenylphosphorane is added 6.0 g. of 1-formylmethyl-2α-carboxy-3α-(1-hydroxyethyl)-5-oxocyclopentane-5-cyclic ethylene acetal-γ-lactone in 25 ml. of benzene. The mixture is stirred at 25° for 2 hours. It is then added to 300 ml. conc. aqueous $NaH_2PO_4$ solution. The mixture is extracted with 2:1 benzene:ethyl acetate. The latter extract is washed with sat. aqueous NaCl, dried over $Na_2SO_4$ and concentrated to dryness. The residue is chromatographed on 420 g. silica gel eluting with 10% acetone in chloroform to give the title product as a viscous pale yellow oil having a cis:trans ratio of 2.3 (nmr); ir $(CHCl_3)$ 5.65, 6.02, 10.3, 10.55μ; nmr $(CDCl_3)$ δ 1.30 (3H, d, J=6), 3.50 (s, cis $OCH_3$), 3.57 (s, trans $OCH_3$), 3.88 (4H, s), 4.2–5 (2H, m - carbinyl H and vinyl H) 6.03 (d, J=6, cis terminal vinyl H), 6.41 (d, J=12, trans terminal vinyl H).

EXAMPLE 8b

2α-Carboxy-3α-(1-hydroxyethyl)-1-(3-ethylenedioxypropyl)-5-oxocyclopentane-5-cyclic ethylene acetal

II → III

Treatment of 2α-carboxy-3α-(1-hydroxyethyl)-1-(3-methoxy-2-propenyl)-5-oxocyclopentane-5-cyclic ethylene acetal-γ-lactone with ethylene glycol as in Example 7 yields the bis ethylene acetal lactone III ir (CHCl$_3$) 5.65μ; nmr δ 1.43 (3H, d, J=6) 4.05 (8H, broad s), 4.5 (1H, q, J=6, d, J=2), 5.05 (1H, t, J=4); ms m/e 298. Yield 70% from aldehyde I.

EXAMPLE 9

2α-Carboxy-3α-(1,1-dihydroxyethyl)-5-oxo-1β-cyclopentane acetic acid methylester, γ-lactone-5-cyclic ethylene acetal and 3α-acetyl-2α-carboxy-5-oxo-1β-cyclopentane acetic acid methylester-5-cyclic ethylene acetal

10 → 11

A suspension of 2α-carboxy-3α-(1-hydroxyethyl)-1-(2-ethylenedioxyethyl)-5-oxocyclopentane-5-cyclic ethylene acetal (2.27 g. - 8.0 mmol) in 1M aqueous sodium hydroxide (16 ml.) is stirred at 60°–70° until completely in solution. The pH is adjusted to ~8.5 by bubbling in carbon dioxide at room temperature. The slightly hazy solution is filtered through celite. To the stirred filtrate is added the aqueous RuO$_4$ solution prepared from 10 mg of RuO$_2$ and 0.5 ml. of a solution of 7.02 g. (32.8 mmol) NaIO$_4$ (4.1:1 molar ratio) in 50 ml. of water. When colloidal RuO$_2$ (black) is visible, a few drops of the aqueous NaIO$_4$ is added converting it to yellow RuO$_4$. The process is repeated until all of the NaIO$_4$ has been added at which time the reappearance of RuO$_2$ requires over 3 minutes. The mixture is filtered, the filtrate is made slightly acidic by adding solid NaH$_2$PO$_4$ and it is extracted six times with ethyl acetate. The latter extract is dried over Na$_2$SO$_4$ and concentrated to dryness under reduced pressure to give the product (2.3 g.) as a mixture of lactol and keto acid forms; ir (CHCl$_3$) 2.8–3.4, 5.68–5.80, 10.55μ.

EXAMPLE 9a

2α-Carboxy-3α-(1,1-dihydroxyethyl)-5-oxocyclopentane propionic acid, methylester, γ-lactone-5-cyclic ethylene acetal and 3α-Acetyl-2α-carboxy-5-oxo-1β-cyclopentane propionic acid methylester-5-cyclic ethylene acetal

III → IV

Treatment of 2α-carboxy-3α-(1-hydroxyethyl)-1-(3-ethylenedioxypropyl)-5-oxocyclopentane-5-cyclic ethylene acetal by the procedure of Example 9 yields product as a mixture of lactol and keto forms; ir (CHCl$_3$) 2.7–3.5, 5.7–5.8, 10.55μ.

EXAMPLE 10

3β-acetyl-2α-carboxy-5-oxocyclopentane-1β-acetic acid, methylester 5-cyclic ethylene acetal

11 → 12

To a solution of 2α-carboxy-3α-(1,1-dihydroxyethyl)-5-oxocyclopentane acetic acid methylester, γ-lactone-5-cyclic ethylene acetal and 3α-acetyl-2α-carboxy-5-oxo-1β-cyclopentane acetic acid methylester-5-cyclic ethylene acetal (2.3 g.) in 30 ml. of dry methanol is added 10 ml. of 3.3M methanolic sodium methoxide. The mixture is kept under nitrogen for 18 hours. It is then concentrated to dryness on the water pump. Saturated aqueous NaH$_2$PO$_4$ is added, and the mixture is extracted with ethyl acetate. The organic extract is dried over Na$_2$SO$_4$ and concentrated to dryness under vacuum to give product (2.12 g.) which crystallizes from ether as rectangular prisms, m.p. 85°–86.5°; tlc R$_F$ 0.55 cyclohexane; ethyl acetate; acetic acid - 30:70:2; nmr (CDCl$_3$) δ2.20 (s, 3H), 3.73 (s, 3H), 3.88 (m, 4H), 9.27 (broad s, 1H).

Optical resolution of (±) 3β-Acetyl 2α-carboxy-5-oxocyclopentane-1β-acetic acid methyl ester 5-cyclic ethylene acetal (±) 3β-Acetyl-2α-carboxy-5-oxocyclopentane-1β-acetic acid methyl ester 5-cyclic ethylene acetal (575 mg) and (−) α-methylbenzylamine (250 mg.) are mixed in ether and crystallization induced by cooling and scratching. The precipitated salt is recrystallized three times from ether containing a trace of acetone, m.p. 105°–110°.

The salt is dissolved in benzene and the latter solution extracted with aqueous KHCO$_3$. The aqueous basic extract is washed with ether, acidified by adding powdered NaH$_2$PO$_4$, and extracted with ethyl acetate. The latter extract is washed with 10% aqueous NaH$_2$PO$_4$, dried over Na$_2$SO$_4$, and concentrated to dryness to give (+) 3β-acetyl 2α-carboxy-5-oxocyclopentane-1β-acetic acid methyl ester 5-cyclic ethylene acetal α$_D^{Chf}$ + 15°.

Repetition of this process with (+) α-methylbenzylamine yields the (−) antipode α$_D^{Chf}$ − 15°.

EXAMPLE 10a

3β-Acetyl-2α-carboxy-5-oxocyclopentane-1β-propionic acid, methylester 5-cyclic ethylene acetal

IV → V

Treatment of the product of Example 9a by the procedure of Example 10 yields acetyl monoester V (yield from III 65%) m.p. 66°–68°; ir 2.8–3.3, 5.72, 5.78, 5.85, 10.5μ, nmr 2.20 (3H,s), 3.70 (3H,s), 3.93 (4H,s), 10.7 (1H broad s); ms m/e 300.

Optical resolution of (±) 3β-Acetyl-2α-carboxy-5-oxocyclopentane-1β-propionic acid methyl ester 5-cyclic ethylene acetal (+) 3β-Acetyl-2α-carboxy-5-oxocyclopentane-1β-propionic acid methyl ester 5-cyclic ethylene acetal (600 mg.) and 1(−) ephedrine (330 mg.) are mixed in ether. Crystallization in induced by scratching with a glass rod and cooling. The precipitated salt is recrystallized twice from ether containing a trace of acetone to yield colorless needles m.p. 128–131°; α$_D^{Chf}$ − 7.2°.

The salt is dissolved in benzene - ethyl acetate and the latter solution extracted with aqueous KHCO$_3$ solution. The aqueous basic extract is washed with ether, acidified by adding powdered NaH$_2$PO$_4$, and finally extracted with ethyl acetate. The latter extract is washed with 10% aqueous NaH$_2$PO$_4$, dried over Na$_2$SO$_4$, and concentrated to dryness to give (+) 3β-acetyl-2α-carboxy-5-oxocyclopentane-1β-propionic acid methyl ester 5-cyclic ethylene acetal α$_D^{Chf}$ + 12.3°.

Repetition of this process with d(+) ephedrine yields the (−) antipode α$_D^{Chf}$ − 12.0°.

EXAMPLE 11

3β-Acetoxy-2α-carboxy-5-oxocyclopentane-1β-acetic acid, methyl ester 5-cyclic ethylene acetal

12 → 13

To a stirred solution of 3β-acetyl-2α-carboxy-5-oxocyclopentane-1β-acetic acid, methylester 5-cyclic ethylene acetal (350 mg.) in $CH_2Cl_2$ (5 ml.) is added 8 g. powdered $Na_2HPO_4$. The stirred mixture is cooled to 0° and 10 ml. of 0.5M peroxytrifluoracetic acid in $CH_2Cl_2$ buffered with powdered $Na_2HPO_4$ is added over 2–3 minutes. The mixture is stirred at room temperature. After 6 hours, a second addition of 10 ml. 0.5M peroxytrifluoracetic acid is made followed by a third addition after an additional 18 hours. After an additional 24 hours, the mixture is concentrated to a small volume, 40 ml. of saturated aqueous $NaH_2PO_4$ is added and the mixture is thoroughly extracted with ethyl acetate. The latter extract is washed with sodium bisulfite (to remove traces of peroxidic material), saturated aqueous sodium chloride, dried over sodium sulfate, and taken to dryness under reduced pressure. Crystallization of the residue (~270 mg.) from ether gives 3β-aceytoxy-2α-carboxy-5-oxocyclopentane-1β-acetic acid, methyl ester 5-cyclic ethylene acetal, m.p. 88°–91°.

EXAMPLE 11a

3β-Acetoxy-2α-carboxy-5-oxocyclopentane-1β-propionic acid, methyl ester 5-cyclic ethylene acetal

V → VI

By the procedure of Example 11, 3β-acetyl-2α-carboxy-5-oxocyclopentane-1β-propionic acid, methylester 5-cyclic ethylene acetal was converted to 3β-acetoxy-2α-carboxy-5-oxocyclopentane-1β-propionic acid, methyl ester 5-cyclic ethylene acetal (yield 75–80%) m.p. 116°–118°; ir ($CHCl_3$) 2.7–3.3, 5.72–5.80, 8.1, 10.55μ; nmr ($CDCl_3$) 2.03 (3H, s), 3.62 (3H, s), 3.92 (4H, s), 5.20 (1H, m), 10.3 (1H, s); ms m/e 316.

EXAMPLE 12

3β-Acetoxy-2α-imidazoylformyl-5-oxocyclopentane-1β-acetic acid, methyl ester 5-cyclic ethylene acetal
and
3β-acetoxy-2α-formyl-5-oxocyclopentane-1β-acetic acid, methyl ester 5-cyclic ethylene acetal

13 → 14 → 15

N,N'-Carbonyldiimidazole (340 mg., 2.1 mmol) is added to a stirred solution of 13 (600 mg., 2.00 mmol) in 10 ml. tetrahydrofuran at 20° under nitrogen. After 3 hours, the solvent is removed under vacuum and the residue taken up to 1;1 benzene-ethyl acetate. The latter solution is washed with saturated aqueous sodium chloride, dried over $Na_2SO_4$, and concentrated to dryness under vacuum to give 3β-acetoxy-2α-imidazoyl-formyl-5-oxocyclopentane-1β-acetic acid, methyl ester 5-cyclic ethylene acetal (690 mg.).

A solution of lithium tri-t-butoxy aluminum hydride (1.02 g., 4 mmol) in 15 ml. tetrahydrofuran is added dropwise to a stirred solution of imidazolide 14 (680 mg., 1.9 mmol) in 10 ml. tetrahydrofuran at 20° under $N_2$. After 4 hours, the mixture is added to a chilled mixture of saturated aqueous $NaH_2PO_4$ and ethyl acetate, and concentrated to remove THF. The mixture is extracted with additional ethyl acetate. The organic phase is washed with brine, dried over $Na_2SO_4$, and concentrated under vacuum to give 3β-acetoxy-2α-formyl-5-oxocyclopentane-1β-acetic acid, methyl ester 5-cyclic ethylene acetal (530 mg.).

EXAMPLE 13

3β-Acetoxy-2α-(3-oxo-1-octenyl)-5-oxocyclopentane-1β-acetic acid, methyl ester 5-cyclic ethylene acetal

15 → 16

A solution of dimethyl 2-oxoheptylphosphonate (444 mg., 2.0 mmol) in 10 ml. dry THF is added dropwise to a stirred suspension of NaH (50% oil dispersion 87 mg., 1.8 mmol) in 15 ml. dry THF at 0° under $N_2$. The ylid sodium salt precipitates in part as a gelatinous white precipitate. After 30 minutes at 0°, a solution of 3β-acetoxy-1α-formyl-5-oxocyclopentane-1β-acetic acid, methyl ester 5-cyclic ethylene acetal (515 mg., 1.8 mmol) in 15 ml. THF is added over 5 minutes. The stirred reaction mixture is allowed to warm to room temperature and stirred for 3 hours, at which time tlc (10% acetone in chloroform) indicates disappearance of starting material. The reaction mixture is cooled to 0°, added to chilled saturated $NaH_2PO_4$, concentrated under vacuum to remove THF, and extracted with ethyl acetate. The latter extract is washed with brine, dried over $Na_2SO_4$, and concentrated to dryness under vacuum. The residue is chromatographed over 50 g. of silica gel eluting with 5% acetone in chloroform to provide pure 3β-acetoxy-2α-(3-oxo-1-octenyl)-5-oxocyclopentane-1β-acetic acid, methyl ester 5-cyclic ethylene acetal.

EXAMPLE 13a

3β-Acetoxy-2α-(7-carbomethoxy-3-oxo-1-heptenyl)-5-oxocyclopentane-1β-propionic acid, methyl ester 5-cyclic ethylene acetal

VI → VII → VIII → IX

By the procedures of Examples 12 and 13, but substituting X in place of dimethyl 2-oxoheptylphosphonate ($PGE_2$ route), VI was converted to VII, VIII, and thence IX (yield from VI 75–80%) $\lambda_{max}^{CH_3OH}$ 225 nm (ε m 12,900); ir ($CHCl_3$) 5.72, 5.80, 5.90, 6.00, 6.15, 8.1, 10.2, 10.55μ; nmr δ 2.02 (3H, s), 3.68 (3H, s), 3.93 (4H, s), 4.92 (1H, broad g, J=8), 6.13 (1H, d, J=16), 6.75 (1H, d, J=16, d, J=8); ms m/e 440.

EXAMPLE 14

3β-Acetoxy-2α-(3S-hydroxy-1-octenyl)-5-oxocyclopentane-1β-acetic acid, methyl ester 5-cyclic ethylene acetal

16 → 17

To a stirred solution of 3β-acetoxy-2-(3-oxo-1-octenyl)-5-oxocyclopentane-1β-acetic acid, methyl ester 5-cyclic ethylene acetal (300 mg) in 7 ml. of methanol at −5° under $N_2$ is added a chilled solution of 30 mg. of sodium borohydride in 3 ml. of methanol. After 30 minutes at −5°, the mixture is added to ice-cold saturated $NaH_2PO_4$ solution (50 ml.) and extracted with ethyl acetate. The extract is dried over $Na_2SO_4$ and concentrated to dryness under water-pump vacuum. The residue is chromatographed over 35 g. of silica gel eluting with 15% acetone-chloroform to give pure 3β-acetoxy-2α-(3-hydroxy-1-octenyl)-5-oxocyclopentane-1β-acetic acid, methyl ester 5-cyclic ethylene acetal. From the later fractions, the epimeric-2α-(3R-hydroxy-1-octenyl) alcohol is obtained.

EXAMPLE 15

3β-Hydroxy-2α-(3S-hydroxy-1-octenyl)-5-oxocyclopentane-1β-acetic acid, 5-cyclic ethylene acetal

17 → 18

To a stirred solution of 3β-acetoxy-2α-(3S-hydroxyl-1-octenyl)-5-oxocyclopentane-1β-acetic acid, methyl ester 5-cyclic ethylene acetal (300 mg) in 8 ml. of methanol under $N_2$ at 0° added dropwise a solution of KOH (300 mg.) in 20 ml. of water. The mixture is kept at 20°–25° for 3 hours. Methanol is removed on the water pump, water is added, and traces of neutral material removed by extraction with ether hexane 1:1. Powdered $NaH_2PO_4$ is added to pH 5, and the mixture is extracted with ethyl acetate. The latter extract is dried over $Na_2SO_4$ and concentrated to dryness under vacuum to give substantially pure dihydroxy acid 3β-hydroxy-2α-(3S-hydroxy-1-octenyl)-5-oxocyclopentane-1β-acetic acid, 5-cyclic ethylene acetal.

EXAMPLE 16

3β-hydroxy-2α-(3S-hydroxy-1-octenyl)-5-oxocyclopentane-1β-acetaldehyde, 5-cyclic ethylene acetal

18 → 19

Compound 18 is converted into aldehyde 19 by the procedure of Example 12.

EXAMPLE 17

3β-Hydroxy-2α-(3S-hydroxy-1-octenyl)-1β-cyclopentanehept-5-enoic acid 5-cyclic ethylene acetal (prostaglandin $E_2$ ethylene acetal)

19 → 20

Sodium hydride-50% mineral oil dispersion (144 mg., 3.0 mmol) is triturated with hexane and the latter decanted to remove the mineral oil. Dimethyl sulfoxide (5 ml.) is added and the mixture kept at 65°–70° under $N_2$ until homogeneous. The stirred solution is cooled to 20°, and 4-carboxybutyl triphenylphosphonium bromide (444 mg., 1.0 mmol) is added. After 30 minutes, a solution of 19 (312 mg., 1.0 mmol) in 5 ml. of dimethyl sulfoxide is added, and the mixture stirred at room temperature overnight. It is then added to cold sat. aq. $NaH_2PO_4$ and extracted with ether. The ether extract is washed with cold dilute NaOH. The aqueous extract is acidified by adding solid powdered $NaH_2PO_4$ and extracted with ethyl acetate. The latter extract is dried over $Na_2SO_4$ and concentrated to dryness under vacuum. The residue is purified by chromatography over 20 g. of silica gel eluting with ethyl acetate-acetone-acetic acid 90:10:1 to give pure 3β-hydroxy-2α-(3S-hydroxy-1-octenyl)-1β-cyclopentanehept-5-enoic acid 5-cyclic ethylene acetal.

EXAMPLE 18

Prostaglandin $E_2$

20 → 21 $PGE_2$

A solution of 3β-hydroxy-2α-(3S-hydroxy-1-octenyl)-1β-cyclopentanehept-5-enoic acid 5-cyclic ethylene acetal (200 mg.) in 1:1 acetic acid-water (20 ml.) is kept at 25° for 3 hours. Cold conc. $NaH_2PO_4$ is added, and the mixture extracted with ethyl acetate. The latter extract is washed with saturated brine solution and dried over $Na_2SO_4$. Toluene is added, and the solution concentrated to dryness under vacuum (<25°) to give (±) $PGE_2$ as a colorless oil.

Repetition of the above experiments beginning with the resolved 3β-acetyl-2α-carboxy-5-oxocyclopentane-1β-acetic acid, methylester 5-cyclic ethylene acetal having a (+) rotation produces $PGE_2$ having the identical stereoconfiguration as the naturally-occurring isomer.

EXAMPLE 19

3β-Acetoxy-2α-(7-carbomethoxy-3-oxo-heptanyl)-5-oxocyclopentane-1β-propionic acid, methyl ester 5-cyclic ethylene acetal

IX → XI

A solution of IX (170 mg.) in ethyl acetate (5 ml.) is added to a prereduced suspension of 10% Pd/C catalyst (70 mg.) in ethyl acetate (5 ml.), and the mixture stirred under $H_2$ at 1 Atm pressure at 25°. Saturation is complete within 5 minutes, the mixture is filtered, and concentrated to dryness to give XI (170 mg.) ir ($CHCl_3$) 5.75, 5.80, 8.1, 10.55μ; nmr ($CDCl_3$) δ2.02 (3H, s), 3.67 (6H, s), 3.93 (4H, s), 4.88 (1H, m); ms m/e 442.

EXAMPLE 20

3β-Hydroxy-2α-(7-carboxy-3-oxoheptanyl)-5-oxocyclopentane-1β-propionic acid 5-cyclic ethylene acetal By the procedure of Example 15, XI is converted into XII m.p. 103°–104°; ir ($CHCl_3$) 1.8–3.3, 5.80, 5.85, 10.60μ; ms m/e of trimethylsilyl derivative 588.

EXAMPLE 21

7α-Hydroxy-5,11-diketo-tetranor-prosta-1,16-dioic acid

By the procedure of Example 18, 3β-hydroxy-2α-(7-carboxy-3-oxo-heptanyl)-5-oxocyclopentane-1β-propionic acid 5-cyclic ethylene acetal is converted into 7α-hydroxy-5,11-diketo-tetranorprosta-1,16-dioic acid, m.p. 101°–102°; ir ($CHCl_3$) ms of dimethyl ester trimethyl silyl ether methoxime identical with that of the natural product (yield 70–75% from IX).

EXAMPLE 22

Prostaglandin $E_1$ Intermediate

A mixture of sodium hydride (192 mg.) and dimethyl sulfoxide is stirred under nitrogen at 65°–70° for 40 minutes. The solution is cooled to 15°–20°, and a solution of 4-carboxybutyl triphenylphosphonium bromide (1.77 g.) in dimethyl sulfoxide (5 ml.) is added. The dark red solution is stirred for 30 minutes, and a solution of compound 9 (500 mg.) in dimethylsulfoxide (4 ml.) is then added. The reaction mixture is stirred at room temperature for 18 hours. It is then added to 10% aqueous $NaH_2PO_4$ and extracted with ether. The ether extract in turn is extracted with 0.5N sodium hydroxide solution. The latter extract is washed with ether, acidified by adding powdered $NaH_2PO_4$, and extracted with ethyl acetate. The ethyl acetate extract is dried over sodium sulfate and concentrated to dryness under vacuum. The residue is dissolved in ether, an excess of an ether solution of diazomethane is added, and after 5 minutes, the mixture is taken to dryness under vacuum. The product is purified by dry-column chromatography on silica gel (38 g.), eluting with 9% acetone in chloroform to give 250 mg. of pure 2α-carboxy-3α-(1-hydroxyethyl)-5-oxocyclopentanehept-5-enoic acid methyl ester 5-cyclic ethylene acetal γ-lactone; ir ($CHCl_3$) 5.68, 5.78, 10.55μ; nmr ($CDCl_3$) δ 1.37 (3H, d, J=6), 3.70 (3H, s), 3.95 (4H, s), 4.47 (1H, m), 5.53 (2H, m); ms M+ 338.

This substance (210 mg) in 10 ml. of ethyl acetate is hydrogenated at 25° and 1 Atm over 50 mg. of 10% palladium on charcoal catalyst. On cessation of hydrogen uptake, the catalyst is removed by filtration, and the filtrate is taken to dryness to give 210 mg. of pure 2α-carboxy-3α-(2-hydroxyethyl)-5-oxocyclopentaneheptanoic acid methyl ester 5-cyclic ethylene acetal, γ-lactone identical with an authentic sample [C. H. Kuo, D. Taub, and N. L. Wendler, Tetrahedron Letters, 5317 (1972)] that has been converted to prostaglandin $E_1$.

EXAMPLE 23

Method of preparing isotopically labelled (deuterium, tritium labelled)
7α-hydroxy-5,11-diketotetranor-prostane-1,16-dioic acid In the hydrogenation of the side chain double bond (Example 19), use of deuterium or tritium in place of hydrogen produces 3β-acetoxy-2α-(7-carbomethoxy-1,2-$D_2$ or 1,2-$T_2$ 3-oxoheptanyl)-5-oxocyclopentane propionic acid 5-cyclic ethylene acetal methyl ester. Hydrolysis of the ester functions in a mixture of $KOD$-$CH_3OD$; $KOT$-$CH_3OT$ introduces deuterium and tritium at the sites adjacent to carbonyl functionality. Labelling is retained in the final product on removal of the ethylene acetal function in aqueous acetic acid. The labelled compounds have the structural formula shown below.

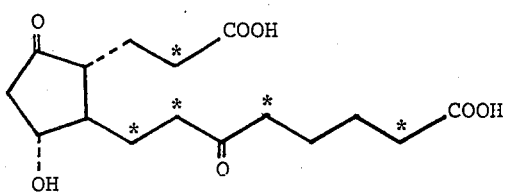

EXAMPLE 24

Dimethyl 2-oxo-6-carbomethoxy-n-hexylphosphonate

X

To a stirred solution of dimethyl methylphosphonate (31 g.) in THF (500 ml.) under $N_2$ at −78° is added n-butyl lithium in hexane (125 cc of 2M). A solution of monomeric adipic anhydride (32 g.) in THF (50 ml.) is then added. The mixture is stirred 15 minutes at −78°, the cooling bath is removed, and the mixture stirred an additional 15 minutes. The mixture is acidified with dilute HCl and extracted with ether thoroughly. The ether extract is washed with water and saturated aqueous NaCl, dried over $MgSO_4$, and concentrated to dryness. The product is dissolved in ether (50 ml.) and esterified with ethereal diazomethane. The crude methyl ester is purified by chromatography on silica gel (1000 g.), eluting with 25% acetone in chloroform. Alternatively, purification is achieved by vacuum distillation, b.p. 100°–105°/0.04 mm.; nmr δ 1.67 (4H, m), 2.37 (2H, m), 2.70 (2H, m), 3.15 (2H, d, J=22), 3.72 (6H, s), 3.92 (3H, s).

What is claimed is:

1. The process for the production of a compound of the formula

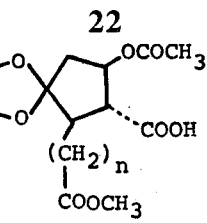

wherein n is 1 or 2 which comprises oxidizing a compound of the formula

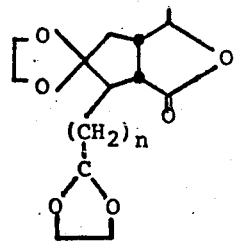

to produce a compound of the formula

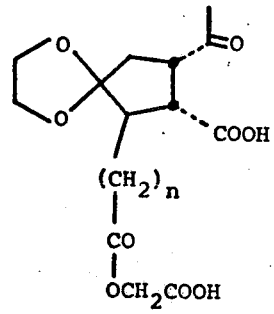

contacting said compound with sodium methoxide in methanol to produce a monoester of the formula

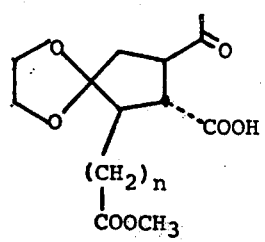

and oxidizing said monoester with peroxytrifluoroacetic acid.

2. A compound selected from the group consisting of:
   3β-acetoxy-2α-carboxy-5-oxocyclopentane-1β-acetic acid, methyl ester 5-cyclic ethylene acetal; or
   3β-acetoxy-2α-carboxy-5-oxocyclopentane-1β-propionic acid, methyl ester 5-cyclic ethylene acetal.

3. A compound according to claim 2 comprising 3β-acetoxy-2α-carboxy-5-oxocyclopentane-1β-acetic acid, methyl ester 5-cyclic ethylene acetal.

* * * * *